United States Patent
Bai et al.

(10) Patent No.: US 11,473,098 B2
(45) Date of Patent: Oct. 18, 2022

(54) TOBACCO ARSENIC TRANSPORT GENE NTNIP7-1 AND CLONING METHOD AND APPLICATIONS THEREOF

(71) Applicant: YUNNAN ACADEMY OF TOBACCO AGRICULTURE SCIENCE, Yunan (CN)

(72) Inventors: Ge Bai, Yunan (CN); Dahai Yang, Yunan (CN); Tao Pang, Yunan (CN); He Xie, Yunan (CN); Yong Li, Yunan (CN); Heng Yao, Yunan (CN); Yongping Li, Yunan (CN); Xuejun Chen, Yunan (CN); Bingguang Xia, Yunan (CN); Dunhuang Fang, Yunan (CN); Yahui Wang, Yunan (CN); Chunjiang Yang, Yunan (CN); Chendong Zhang, Yunan (CN); Xingfu Wu, Yunan (CN); Jianmin Zeng, Yunan (CN)

(73) Assignee: YUNAN ACADEMY OF TOBACCO AGRICULTURE SCIENCE, Yunan (CN)

( * ) Notice: Subject to any disclaimer, the term of this patent is extended or adjusted under 35 U.S.C. 154(b) by 175 days.

(21) Appl. No.: 16/581,671

(22) Filed: Sep. 24, 2019

(65) Prior Publication Data

US 2020/0140878 A1    May 7, 2020

(30) Foreign Application Priority Data

Nov. 17, 2018  (CN) .......................... 201811369666.9

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

PUBLICATIONS

Chen, Aiqun, et al. (New Phytologist 173.4 (2007): 817-831). (Year: 2007).*
Kramer, et al. ("Enzymatic Amplification of DNA by PCR: Standard Procedures and Optimization." Current Protocols in Cell Biology 10.1 (2001): A-3F). (Year: 2001).*
GenBank Accession XM_009625098, dated Oct. 14, 2014. (Year: 2014).*

* cited by examiner

*Primary Examiner* — Charles Logsdon (57) ABSTRACT

A tobacco arsenic transport gene NtNIP7-1 and a cloning method and application thereof are disclosed. A nucleotide sequence of the tobacco arsenic transport gene NtNIP7-1 is shown as SEQ ID: No. 1, and an encoded amino acid sequence thereof is shown as SEQ ID: No. 2. The cloning method of the tobacco arsenic transport gene NtNIP7-1 includes (S1) extracting RNA in tobacco, performing reverse transcription, and obtaining a first-strand cDNA; and (S2) taking the first-strand cDNA obtained by the reverse transcription as a template, synthesizing a specific primer according to sequences of the NtNIP7-1 gene, performing PCR amplification, recovering and purifying a product of the PCR amplification, and sequencing. In the present invention, inhibition of the expression of the tobacco endogenous gene NtNIP7-1 in tobacco plants is able to significantly reduce the arsenic content of tobacco leaves, and has broad application prospects in the field of low arsenic content breeding.

2 Claims, 4 Drawing Sheets

Specification includes a Sequence Listing.

SEQUENCE LISTING

<160> NUMBER OF SEQ ID NOS: 12

<210> SEQ ID NO 1
<211> LENGTH: 1608
<212> TYPE: DNA
<213> ORGANISM: Artificial sequence
<220> FEATURE:
<223> OTHER INFORMATION: Synthesis

<400> SEQUENCE: 1

```
atggctaaag atcaattgca agtgctaaat gcactagatg tagcaaaaac acaattgtac      60
catttcactg caattgtaat tgctggaatg ggatttttta ctgatgccta tgacctttt     120 tgcatttcac tagtcacaaa attacttggc cgaatttatt atcatcacga aaatgcacca     180
aaaccaggta ttctccctcc tcctatcgca gctgctgtta atggcgtcgc gtttgttggt     240
actctttcgg ggcaactgtt tttcgggtgg ctaggagata aattagggag gaaaaaagtt     300
tatggaatga cacttatgct tatggttatt tgttcaatag cttctggact ttcttttggt     360
aaaacaccta atggtgttat agccactta tgttttttc gattttggct tggttttggt     420
attggtggcg attacccttt atccgcgaca attatgtctg aatatgcaaa taaaaaaact     480
cgtggggctt ttattgctgc tgttttgca atgcaaggtt ttggtatttt agcaggcgga     540
atagttgcac ttattgttgc tggtgcattt aaaaatgctt accttcacc aatttattca     600 gtaaatccta aagattcaac accacctgaa gctgattatg tttggagaat tattgtaatg     660
tttggtgcaa ttccagcttt acttacttat tactggcgaa tgaagatgcc cgaaacagca     720
cgttacacgg ccttagttgc gaaaaatgct gaaaagctg ctgctgatat gtccaaagta     780
ttgaacgttg aaattgaagt agagaaagat aaagttgaag aaaaccgaca tagttttggt     840
ttgtttacta aggaatttct tcgtcgccat ggacttcact tgctaggaac aactagtaca     900
tggtttttat tagatattgc tttttacagt caaaatcttt tcagaagga tatatttagt     960 aaaattggat ggattcctca tccagaaacg atgaatgcat tagatgaagt tttcaagatt    1020
gcaagggcac agactcttat tgcactttgc agtactgttc caggttactg gtttactgta    1080
gcatttatcg ataaaatggg tcgatttgct attcaattaa tgggattctt tttcatgaca    1140
gttttcatgt ttgctttagc cattccatat aatcactgga cacaaaagga aaacagaata    1200
gggtttgtta tcatgtattc acttacgttt ttcttcgcga attttggtcc aaatgcaaca    1260
acatttgttg tacccgcgga gattttttcca gctaggttaa gatcaacgtg ccacggaata    1320
```

```
tcagcagcag ctggaaaagc tggagcaatt gttggggcat ttggattttt gtatgcagct    1380
caatccactg atccattaaa ggttgatgct ggttatccaa ctggtatagg tgtgaaaaat    1440
gcacttattg ttcttggttg tgttaattta cttggaatgt tgtttacatt cttggtgcca    1500
gaatccaaag gaaaatcatt ggaggaaatg tctaaggaaa atgaaagaga agaagaaaat    1560
tatgaaacag aatctaaggc agataatgca caaacaattc cagtttaa                 1608
```

<210> SEQ ID NO 2
<211> LENGTH: 535
<212> TYPE: PRT
<213> ORGANISM: Artificial sequence
<220> FEATURE:
<223> OTHER INFORMATION: Synthesis

<400> SEQUENCE: 2

```
Met Ala Lys Asp Gln Leu Gln Val Leu Asn Ala Leu Asp Val Ala Lys
1               5                   10                  15

Thr Gln Leu Tyr His Phe Thr Ala Ile Val Ile Ala Gly Met Gly Phe
            20                  25                  30

Phe Thr Asp Ala Tyr Asp Leu Phe Cys Ile Ser Leu Val Thr Lys Leu
        35                  40                  45

Leu Gly Arg Ile Tyr Tyr His His Glu Asn Ala Pro Lys Pro Gly Ile
    50                  55                  60

Leu Pro Pro Ile Ala Ala Val Asn Gly Val Ala Phe Val Gly
65                  70                  75                  80

Thr Leu Ser Gly Gln Leu Phe Phe Gly Trp Leu Gly Asp Lys Leu Gly
                85                  90                  95

Arg Lys Lys Val Tyr Gly Met Thr Leu Met Leu Met Val Ile Cys Ser
            100                 105                 110

Ile Ala Ser Gly Leu Ser Phe Gly Lys Thr Pro Asn Gly Val Ile Ala
        115                 120                 125

Thr Leu Cys Phe Phe Arg Phe Trp Leu Gly Phe Gly Ile Gly Gly Asp
    130                 135                 140

Tyr Pro Leu Ser Ala Thr Ile Met Ser Glu Tyr Ala Asn Lys Lys Thr
145                 150                 155                 160

Arg Gly Ala Phe Ile Ala Ala Val Phe Ala Met Gln Gly Phe Gly Ile
                165                 170                 175

Leu Ala Gly Gly Ile Val Ala Leu Ile Val Ala Gly Ala Phe Lys Asn
            180                 185                 190

Ala Tyr Pro Ser Pro Ile Tyr Ser Val Asn Pro Lys Asp Ser Thr Pro
        195                 200                 205

Pro Glu Ala Asp Tyr Val Trp Arg Ile Ile Val Met Phe Gly Ala Ile
    210                 215                 220

Pro Ala Leu Leu Thr Tyr Tyr Trp Arg Met Lys Met Pro Glu Thr Ala
225                 230                 235                 240

Arg Tyr Thr Ala Leu Val Ala Lys Asn Ala Glu Lys Ala Ala Ala Asp
                245                 250                 255

Met Ser Lys Val Leu Asn Val Glu Ile Glu Val Glu Lys Asp Lys Val
            260                 265                 270

Glu Glu Asn Arg His Ser Phe Gly Leu Phe Thr Lys Glu Phe Leu Arg
        275                 280                 285

Arg His Gly Leu His Leu Leu Gly Thr Thr Ser Thr Trp Phe Leu Leu
    290                 295                 300

Asp Ile Ala Phe Tyr Ser Gln Asn Leu Phe Gln Lys Asp Ile Phe Ser
```

```
            305                 310                 315                 320
Lys Ile Gly Trp Ile Pro His Pro Glu Thr Met Asn Ala Leu Asp Glu
                325                 330                 335

Val Phe Lys Ile Ala Arg Ala Gln Thr Leu Ile Ala Leu Cys Ser Thr
            340                 345                 350

Val Pro Gly Tyr Trp Phe Thr Val Ala Phe Ile Asp Lys Met Gly Arg
        355                 360                 365

Phe Ala Ile Gln Leu Met Gly Phe Phe Met Thr Val Phe Met Phe
    370                 375                 380

Ala Leu Ala Ile Pro Tyr Asn His Trp Thr Gln Lys Glu Asn Arg Ile
385                 390                 395                 400

Gly Phe Val Ile Met Tyr Ser Leu Thr Phe Phe Ala Asn Phe Gly
                405                 410                 415

Pro Asn Ala Thr Thr Phe Val Val Pro Ala Glu Ile Phe Pro Ala Arg
                420                 425                 430

Leu Arg Ser Thr Cys His Gly Ile Ser Ala Ala Gly Lys Ala Gly
                435                 440                 445

Ala Ile Val Gly Ala Phe Gly Phe Leu Tyr Ala Ala Gln Ser Thr Asp
    450                 455                 460

Pro Leu Lys Val Asp Ala Gly Tyr Pro Thr Gly Ile Gly Val Lys Asn
465                 470                 475                 480

Ala Leu Ile Val Leu Gly Cys Val Asn Leu Leu Gly Met Leu Phe Thr
                485                 490                 495

Phe Leu Val Pro Glu Ser Lys Gly Lys Ser Leu Glu Glu Met Ser Lys
                500                 505                 510

Glu Asn Glu Arg Glu Glu Glu Asn Tyr Glu Thr Glu Ser Lys Ala Asp
            515                 520                 525

Asn Ala Gln Thr Ile Pro Val
            530                 535

<210> SEQ ID NO 3
<211> LENGTH: 25
<212> TYPE: DNA
<213> ORGANISM: Artificial sequence
<220> FEATURE:
<223> OTHER INFORMATION: Synthesis

<400> SEQUENCE: 3
atggctaaag atcaattgca agtgc                                        25

<210> SEQ ID NO 4
<211> LENGTH: 26
<212> TYPE: DNA
<213> ORGANISM: Artificial sequence
<220> FEATURE:
<223> OTHER INFORMATION: Synthesis

<400> SEQUENCE: 4
ttaaactgga attgtttgtg cattat                                       26

<210> SEQ ID NO 5
<211> LENGTH: 55
<212> TYPE: DNA
<213> ORGANISM: Artificial sequence
<220> FEATURE:
<223> OTHER INFORMATION: Synthesis

<400> SEQUENCE: 5
ggggacaagt ttgtacaaaa aagcaggctg ctcacgaaaa tgcaccaaaa ccagg        55
```

```
<210> SEQ ID NO 6
<211> LENGTH: 56
<212> TYPE: DNA
<213> ORGANISM: Artificial sequence
<220> FEATURE:
<223> OTHER INFORMATION: Synthesis

<400> SEQUENCE: 6
ggggaccact tgtacaaga aagctgggtc gataaagggt aatcgccacc aatacc      56

<210> SEQ ID NO 7
<211> LENGTH: 20
<212> TYPE: DNA
<213> ORGANISM: Artificial sequence
<220> FEATURE:
<223> OTHER INFORMATION: Synthesis

<400> SEQUENCE: 7
tctggacgaa gagcatcagg                                             20

<210> SEQ ID NO 8
<211> LENGTH: 20
<212> TYPE: DNA
<213> ORGANISM: Artificial sequence
<220> FEATURE:
<223> OTHER INFORMATION: Synthesis

<400> SEQUENCE: 8
atgaatccag aaaagcggcc                                             20

<210> SEQ ID NO 9
<211> LENGTH: 20
<212> TYPE: DNA
<213> ORGANISM: Artificial sequence
<220> FEATURE:
<223> OTHER INFORMATION: Synthesis

<400> SEQUENCE: 9
aggtccagtc tgttgtgagg                                             20

<210> SEQ ID NO 10
<211> LENGTH: 20
<212> TYPE: DNA
<213> ORGANISM: Artificial sequence
<220> FEATURE:
<223> OTHER INFORMATION: Synthesis

<400> SEQUENCE: 10
tttgccttaa cccgttgagc                                             20

<210> SEQ ID NO 11
<211> LENGTH: 20
<212> TYPE: DNA
<213> ORGANISM: Artificial sequence
<220> FEATURE:
<223> OTHER INFORMATION: Synthesis

<400> SEQUENCE: 11
gaagaaggtc ccaagggttc                                             20

<210> SEQ ID NO 12
<211> LENGTH: 20
<212> TYPE: DNA
<213> ORGANISM: Artificial sequence
<220> FEATURE:
```

-continued

<223> OTHER INFORMATION: Synthesis

<400> SEQUENCE: 12
tctcccttta acaccaacgg                    20

TOBACCO ARSENIC TRANSPORT GENE NTNIP7-1 AND CLONING METHOD AND APPLICATIONS THEREOF

CROSS REFERENCE OF RELATED APPLICATION

The present invention claims priority under 35 U.S.C. 119(a-d) to CN 201811369666.9, filed Nov. 17, 2018.

INCORPORATION-BY-REFERENCE OF THE SEQUENCE LISTING

The Sequence Listing associated with this application is provided in text file, and is hereby incorporated by reference into the specification. The name of the text file containing the Sequence Listing is BJP599Sequencelisting.txt. The text file is 9 KB, was created on Sep. 16, 2020, and is being submitted electronically via EFS-Web.

BACKGROUND OF THE PRESENT INVENTION

Field of Invention

The present invention relates to the field of genetic engineering technology, and more particularly to a tobacco arsenic transport gene NtNIP7-1 and its cloning method and applications.

Description of Related Arts

Arsenic is widely found in nature, and is one of the most abundant elements in the crust with an average concentration close to 3 mg/kg (Cullen and Reimer, 1989). Usually, arsenic is released into the environment through natural reactions and human actions, such as volcanic emissions, rock weathering, hot spring release, mining, smelting, and the use of arsenic-containing pesticides, herbicides, wood preservatives and feed additives (Zhao et Al., 2010b). At present, arsenic pollution has become a global problem, and is mainly related to food, air, water and soil pollution. Inorganic arsenic is a human primary carcinogen, and water and food are the main sources of arsenic contamination (Smith et al., 2002; Tsuji et al., 2007). Reports show that groundwater in more than 70 countries is contaminated with arsenic, which is a serious health hazard to about 150 million people around the world. About 110 million of these people come from ten countries in Asia. At present, China is the second most serious country for arsenic pollution after Bangladesh. The toxic intensity of arsenic is related to the form of existence. The toxicity of inorganic arsenic is higher than that of organic arsenic. The toxicity of arsenite is higher than that of arsenate in inorganic arsenic, but when the pentavalent arsenic of monomethyl arsenate (MMA) and dimethyl arsenate (DMA) is reduced to trivalent arsenic in organic arsenic, the toxicity is significantly increased (Styblo et al., 2000). The harm of arsenic to animals and plants is enormous, and when the arsenic concentration exceeds a certain range, plants will die. For example, long-term exposure to arsenic easily causes photosynthesis to be blocked, growth and development to be inhibited, and grain yield reduction (Jain and Gadre, 1997). The human body may cause diseases such as skin, digestive system, nervous system, respiratory system and cardiovascular system after arsenism (Kala et al., 2000; Mao et al., 2010). Tobacco is an important economic crop that is widely cultivated in China. If tobacco is grown in arsenic-rich soils, arsenic is able to be enriched; and after being enriched in arsenic, tobacco is processed into cigarette products, which may endanger the health of consumers. Accordingly, in the process of tobacco planting, the problem of excessive arsenic content needs to be solved, and it is difficult to reduce the arsenic content in tobacco by agronomic methods. Therefore, it is a more effective way to genetically improve tobacco for reducing the arsenic content. The NIP7-1 gene previously had the function of absorbing arsenic in other species, but its function in tobacco has not been reported.

SUMMARY OF THE PRESENT INVENTION

A first object of the present invention is to provide a tobacco arsenic transport gene NtNIP7-1, a second object of the present invention is to provide a cloning method of the tobacco arsenic transport gene NtNIP7-1, a third object of the present invention is to provide applications of the tobacco arsenic transport gene NtNIP7-1.

The first object of the present invention is achieved as follows. A nucleotide sequence of the tobacco arsenic transport gene NtNIP7-1 is shown as SEQ ID NO: 1.

The second object of the present invention is achieved as follows. A cloning method of the tobacco arsenic transport gene NtNIP7-1, which comprises steps of:

(S1) synthesizing a first-strand cDNA (complementary deoxyribonucleic acid) of tobacco, which comprises extracting RNA (ribonucleic acid) of the tobacco, performing reverse transcription, and obtaining the first-strand cDNA; and (S2) taking the first-strand cDNA obtained by the reverse transcription as a template, synthesizing a specific primer according to sequences of the NtNIP7-1 gene, performing PCR (polymerase chain reaction) amplification, recovering and purifying a product of the PCR amplification, and sequencing.

The third object of the present invention is achieved as follows. A preparation method of a low arsenic transgenic plant comprises applying the tobacco arsenic transport gene NtNIP7-1.

Also, the present invention provides a preparation method of a tobacco variety and its seed and asexual propagule comprises applying the tobacco arsenic transport gene NtNIP7-1.

Also, the present invention provides a preparation method of an expression cassette comprises applying the tobacco arsenic transport gene NtNIP7-1.

Also, the present invention provides a preparation method of a transgenic cell line comprises applying the tobacco arsenic transport gene NtNIP7-1.

Also, the present invention provides a preparation method of a recombinant bacteria comprises applying the tobacco arsenic transport gene NtNIP7-1.

The NtNIP7-1 gene is a gene family and has multiple homologous genes in tobacco. The homology of the NtNIP7-1 gene in tobacco is lower than that of other crops. Therefore, it is important to determine that the gene has the function of absorbing arsenic in tobacco. The present invention reduces the expression level of the NtNIP7-1 gene in tobacco for significantly reducing the arsenic content in tobacco, so that the gene is able to be applied to the breeding of low arsenic plant varieties, and has great application prospect and value.

The tobacco arsenic transporter gene NtNIP7-1 provided by the present invention encodes a polypeptide of transporting arsenic ions, wherein the polypeptide comprises an amino acid sequence which is shown as SEQ ID: No. 2. The polypeptide may also be formed by substitution and/or deletion and/or addition of one or more amino acid residues of the amino acid sequence represented by SEQ ID No: 2, and is a derived polypeptide having a function of absorbing arsenic ions. Substitutions and/or deletions and/or additions of the one or more amino acid residues refer to substitutions and/or deletions and/or additions of no more than 10 amino acid residues.

The nucleotide sequence of the tobacco arsenic transport gene NtNIP7-1 provided by the present invention is shown as SEQ ID: No. 1; or is a nucleotide sequence which is able to hybridize with a DNA sequence defined by SEQ ID: No. 1 in the sequence listing under high stringent conditions; or has 70% or more homology with the DNA sequence defined by SEQ ID: No. 1 in the sequence listing, and encodes the DNA sequence with the same functional protein.

An application of the tobacco arsenic transport gene NtNIP7-1 provided by the present invention is as follows. The expression of the NtNIP7-1 gene in tobacco is inhibited to reduce the arsenic content in tobacco. The expression of the NtNIP7-1 gene is able to be inhibited by various methods mediated by RNA, such as a method of mediating gene silencing by plant virus vectors, *Agrobacterium*-mediated transformation of RNAi interference vector, optimization and modification of genetic coding, and optimization of gene promoters. The methods for inhibiting the gene expression provided by the present invention are not limited to the above several methods as long as the expression of the NtNIP7-1 gene is able to be inhibited.

The tobacco arsenic transport gene NtNIP7-1 provided by the present invention and its encoding gene provide gene and technology support for crops, especially low arsenic content breeding of tobacco.

In the present invention, inhibition of the expression of the tobacco arsenic transport gene NtNIP7-1 in tobacco is able to significantly reduce the arsenic content in tobacco, has broad application prospects in the field of low arsenic content breeding, and has great economic benefit potential.

DETAILED DESCRIPTION OF THE PREFERRED EMBODIMENT

The present invention is further described in detail with accompanying embodiments and drawings as follows, which are not intended to limit the present invention, and any transformations or substitutions made in accordance with the teachings of the present invention are within the protective scope of the present invention.

A nucleotide sequence of a tobacco arsenic transport gene NtNIP7-1 provided by the present invention is shown as SEQ ID NO: 1.

An encoded amino acid sequence of the tobacco arsenic transport gene NtNIP7-1 is shown as SEQ ID NO: 2.

A cloning method of the tobacco arsenic transport gene NtNIP7-1 provided by the present invention comprises steps of:

(S1) synthesizing a first-strand cDNA (complementary deoxyribonucleic acid) of tobacco, which comprises extracting RNA (ribonucleic acid) of the tobacco, performing reverse transcription, and obtaining the first-strand cDNA; and (S2) taking the first-strand cDNA obtained by the reverse transcription as a template, synthesizing a specific primer according to sequences of the NtNIP7-1 gene, performing PCR (polymerase chain reaction) amplification, recovering and purifying a product of the PCR amplification, and sequencing.

In the step of (S2), the specific primer comprises:

a forward primer with a sequence of 5'-ATGGCTAAAGA TCAATTGCAAGTGC-3' (SEQ ID NO: 3);
and
a reverse primer with a sequence of 5'-TTAAACTGGAA TTGTTTGTGCATTAT-3' (SEQ ID NO: 4).

In the step of (S2), a reaction system and reaction conditions of the PCR amplification are as follows.

| System of PCR amplification: 50 μL system | | Conditions of PCR amplification | |
|---|---|---|---|
| Template DNA | 1 μL | ① 98° C. | 5 min |
| primer-F (10 μmol/L) | 1 μL | ② 98° C. | 30 s |
| primer-R (10 μmol/L) | 1 μL | ③ 58° C. | 30 s |
| 5 × buffer | 10 μL | ④ 72° C. | 30 s |
| dNTP mixture (10 mmol/L) | 1 μL | ②-④ | 35 cycles |
| Phusion DNA Polymerase | 0.5 μL | ⑤ 72° C. | 5 min |
| ddH$_2$O | Up to 50 μL | 4° C. | Forever |

Also, the present invention provides a preparation method of a low arsenic transgenic plant comprises applying the tobacco arsenic transport gene NtNIP7-1 provided by the present invention.

Also, the present invention provides a preparation method of a tobacco variety and its seed and asexual propagule comprises applying the tobacco arsenic transport gene NtNIP7-1 provided by the present invention.

An application of the tobacco arsenic transport gene NtNIP7-1 provided by the present invention is as follows. The expression of the NtNIP7-1 gene in tobacco is inhibited to reduce the arsenic content in tobacco. The expression of the NtNIP7-1 gene is able to be inhibited by various methods mediated by RNA, such as a method of mediating gene silencing by plant virus vectors, *Agrobacterium*-mediated transformation of RNAi interference vector, optimization and modification of genetic coding, and optimization of gene promoters. The methods for inhibiting the gene expression provided by the present invention are not limited to the above several methods as long as the expression of the NtNIP7-1 gene is able to be inhibited.

The tobacco arsenic transport gene NtNIP7-1 provided by the present invention and its encoding gene provide gene and technology support for crops, especially low arsenic content breeding of tobacco.

In the present invention, inhibition of the expression of the tobacco arsenic transport gene NtNIP7-1 in tobacco is able to significantly reduce the arsenic content in tobacco, has broad application prospects in the field of low arsenic content breeding, and has great economic benefit potential.

The present invention is further explained with specific embodiments as follows.

All plant materials in the embodiments are obtained from *Nicotiana tabacum* variety 'Yunyan 87' and Yunyan 87 transgenic plants with RNAi interfering the expression of the NtNIP7-1 gene. The growth and development stages of tobacco plants are in the artificial climate room and the growth temperature is maintained between 22-25° C. to minimize the influence of external environmental factors on the absorption of arsenic by tobacco. The tobacco materials selected in the experiment are non-transgenic tobacco plants and transgenic tobacco plants with similar developmental phenotype in 6-7 leaf stages. The arsenic solution is added to the soil of the cultivated tobacco to increase the concentration of arsenic ions in the soil, so as to more accurately determine the function of the gene. The leaves with the same leaf position of the non-transgenic tobacco plants and the transgenic tobacco plants are taken for sampling, and these tobacco materials are performed deactivation of enzymes for the arsenic content testing.

First Embodiment

Cloning the NtNIP7-1 Gene:

Taking cDNA of tobacco as a template, designing a primer according to tobacco genome database information, performing PCR (polymerase chain reaction) amplification on the NtNIP7-1 gene, and obtaining a product of the PCR amplification, wherein:

the primer comprises:

a forward primer with a sequence of 5'-ATGGCTAAAGA TCAATTGCAAGTGC-3' (SEQ ID NO: 3); and a reverse primer with a sequence of 5'-TTAAACTGGAA TTGTTTGTGCATTAT-3' (SEQ ID NO: 4).

A reaction system and reaction conditions of the PCR amplification are as follows.

| System of PCR amplification: 50 μL system | | Conditions of PCR amplification | | |
|---|---|---|---|---|
| Template DNA | 1 μL | ① | 98° C. | 5 min |
| primer-F (10 μmol/L) | 1 μL | ② | 98° C. | 30 s |
| primer-R (10 μmol/L) | 1 μL | ③ | 58° C. | 30 s |
| 5 × buffer | 10 μL | ④ | 72° C. | 30 s |
| dNTP mixture (10 mmol/L) | 1 μL | ②-④ | | 35 cycles |
| Phusion DNA Polymerase | 0.5 μL | ⑤ | 72° C. | 5 min |
| ddH$_2$O | Up to 50 μL | | 4° C. | Forever |

Figure 1:
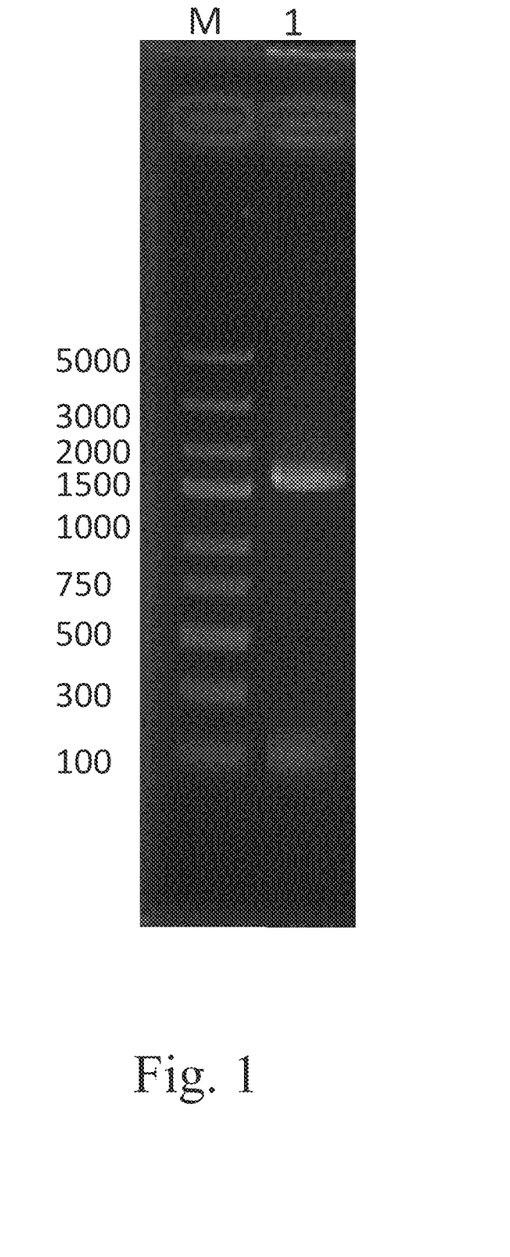
FIG. 1 is an electropherogram of a PCR product of NtNIP7-1 gene, wherein M refers to molecular weight marker and reference numeral 1 refers to PCR product.

The product obtained by the PCR amplification is electrophoresed in a 0.8% agarose gel, and the results of gel electrophoresis are shown in FIG. 1. After the electrophoresis is completed, the product is recovered and purified according to the product description using PCR product purification kits, Qiagen Company, and then are sent to Invitrogen for sequencing to verify sequence results.

Second Embodiment

Construction of Plant RNAi Vector

The full-length fragment of NtNIP7-1 in the first embodiment is used as a template, the PCR amplification is performed with a primer containing a gateway linker sequence, the product of the PCR amplification is purified and then inserted into the pdonr-zeo vector (Invitrogen Company) through BP recombination reaction (referring to FIG. 2), then NtNIP7-1 fragments of the constructed BP reaction vector are replaced into PHellsgate12 RNAi interference vector (referring to FIG. 3) through LR recombination reaction.

(1) Sequences of gateway reaction products are as follows.

```
NtNIP7-1_F:
                                    (SEQ ID NO: 5)
5'-GGGGACAAGTTTGTACAAAAAAGCAGGCTGCTCACGAAAATGCACCA

AAACCAGG-3';

NtNIP7-1_R:
                                    (SEQ ID NO: 6)
5'-GGGGACCACTTTGTACAAGAAAGCTGGGTCgataaagggtaatcgcc accaatacc-3'
```

(2) PCR cloning is performed using Phusion™ high-fidelity polymerase (NEB Company) in the PCR reaction.

Reaction system and conditions of PCR amplification of the second embodiment are as same as those of the first embodiment.

Figure 2:
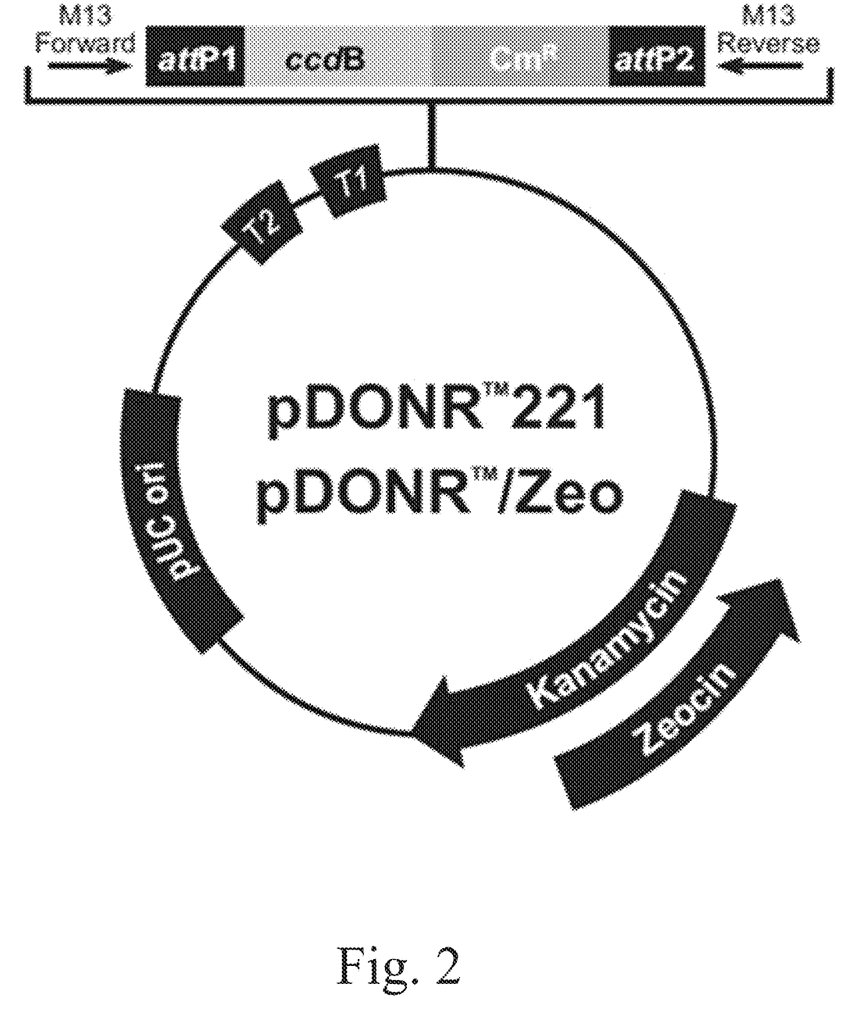
FIG. 2 is a Pdonr-zeo diagram of an intermediate vector.
Figure 3:
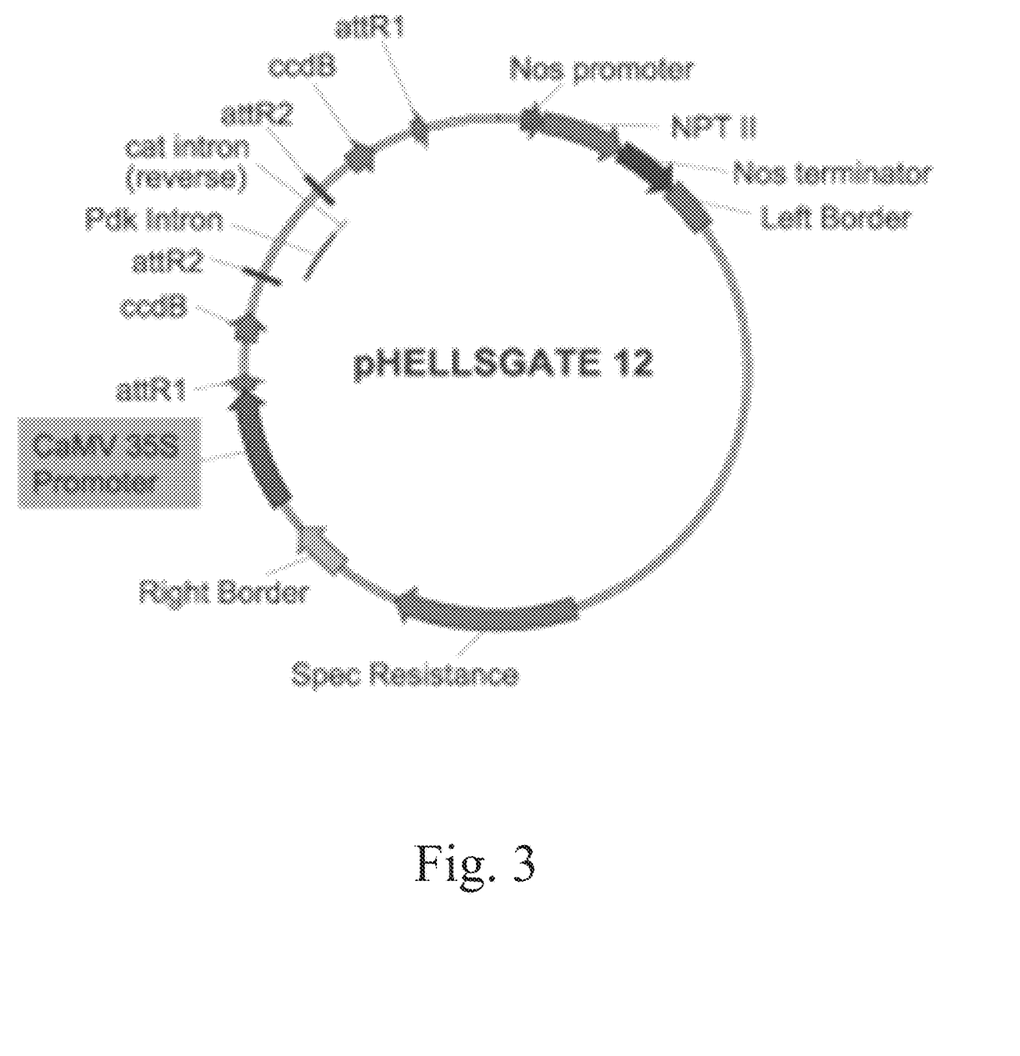
FIG. 3 is a diagram showing the NtNIP7-1 gene plant RNAi interference vector pHellsgate12.

(3) BP Reaction:

(a) Preparing 8 μL of a reaction system in a 200 μL centrifuge tube, which comprises: adding 1-7 μL of attB-PCR product (approximately 15-150 ng, a mass concentration≥10 ng/μL), 1 μL, 150 ng/μL of pDONR-zeo vector and a suitable amount of TE buffer with a pH value of 8.0 into the 200 μL centrifuge tube, and evenly mixing at room temperature;

(b) standing a BP Clonase™ II enzyme mixture on ice for 2 min, melting, and gently shaking for twice;

(c) adding 2 μL of the BP Clonase™ II enzyme mixture into the reaction system obtained by the step of (a), gently mixing, and obtaining an intermediate system;

(d) storing the BP Clonase™ II enzyme mixture at −20° C. or −80° C.;

(e) performing warm bath on the intermediate system at 25° C. for 1 h;

(f) adding 1 μL of proteinase K solution to the intermediate system performed by warm bath, gently shaking, and then performing warm bath at 37° C. for 10 min to terminate the BP reaction, and obtaining a mixture; and (g) after transforming the mixture obtained by the step of (f) into an *Escherichia coli* solution, painting the transformed *Escherichia coli* solution on a Zeacin-resistant LB plate, selecting colonies to a corresponding antibiotic medium solution, performing shake culture, and extracting positive cloned pDONR-Zeocin plasmids (referring to FIG. 2).

(4) LR Reaction:

(a) Preparing 8 μL of a reactant in a 200 μL centrifuge tube, which comprises: adding 1-7 μL of the pDONR-Zeocin plasmids (with a weight in a range of 15-150 ng), 1 μL, 150 ng/μL of destination vector and a suitable amount of TE buffer with a pH value of 8.0 into the 200 μL centrifuge tube, and evenly mixing at room temperature;

(b) standing a LR Clonase™ II enzyme mixture on ice for 2 min, melting, and gently shaking for twice;

(c) adding 2 μL of the LR Clonase™ II enzyme mixture into the reaction system obtained by the step of (a), gently mixing, and obtaining an intermediate system;

(d) storing the LR Clonase™ II enzyme mixture at −20° C. or −80° C. in a refrigerator;

(e) performing warm bath on the intermediate system at 25° C. for 1 h; and (f) adding 1 μL of proteinase K solution to the intermediate system performed by warm bath to termination the LR reaction, gently shaking, standing at 37° C. for 10 min, shaking bacteria and expanding propagation, and obtaining pHellsgate12 RNAi interfere vector.

Third Embodiment

*Agrobacterium*-Mediated Tobacco Transformation and Identification of Transgenic Plants (1) Transformation of *Agrobacterium* by a Freeze-Thaw Method Adding 1 μg of pHellsgate12 recombinant vector with a concentration of 200 ng/μL to 100 μL of competent *Agrobacterium* LBA4404, standing on ice for 5 min after uniformly mixing, freezing in liquid nitrogen for 5 min, taking out from the liquid nitrogen, performing water bath at 37° C. for 5 min in a water bath boiler, standing on ice for 5 min again, adding 500 μL of LB solution, culturing for 4 h at 28° C. under full shaking conditions, obtaining a bacterial solution, evenly painting the bacterial solution on a selective plate medium, and culturing at 28° C. for 48 h.

(2) Leaf disc method for transforming tobacco variety 'Yunyan 87', which comprises steps of:

(a) under aseptic conditions, placing seeds of 'Yunyan 87' in an EP tube and washing the seeds with a first amount of sterile water for 2-3 times;

(b) immersing in 75% alcohol for 30-60 s;

(c) processing with 0.1% mercuric chloride for 5 min, and washing with a second amount of sterile water for 5 times;

(d) sowing on an MS (Murashige & Skoog) medium, performing dark culture for 4 days in Yunnan Academy of Tobacco Agricultural Sciences, China, and performing light culture at 25° C. for 20-30 days;

(e) when seedlings of the tobacco grow to 3-5 cm after 20-30 days, placing terminal buds of the seedlings on an MS+BA (Murashige & Skoog+Benzylaminopurine) medium with a concentration of 0.2 mg/L for rapid growth, and performing subculture;

(f) After 14 days of the subculture, namely, when there are small leaves, selecting the leaves with a size of 1 cm×1 cm, cutting off petioles, leaf surfaces and leaf edge scratches, placing on a MS+BA pre-culture medium with a concentration of 1.0 mg/L and a pH value in a range of 6.0-6.5, wherein the leaves face down and are close to the pre-culture medium, and pre-culturing for 2-3 days in the dark; and (g) taking out the pre-cultured leaves or stems, placing into an *Agrobacterium* infestation solution for infection, wherein at one night before the infection, 2 bottles of *Agrobacterium* are shaken; filling 2 mL centrifuge tube with the *Agrobacterium* infestation solution, centrifuging at 4000 r/min for 5 min, washing twice with a bacterial suspension, wherein the bacterial suspension is added with a ratio of 1:10, Acetosyringone (As) with a concentration of 25 mg/L (that is, 40 mL of As in 40 mL) is added, the infestation solution is shaken for 10 min to sufficiently contact with the leaves and incision of the stems, taking out; placing on a sterilized dry filter paper, and drying;

wherein a preparation method of the *Agrobacterium* infestation solution comprises steps of:

(a') taking *Agrobacterium* which is transformed and stored at −80° C. in a refrigerator, culturing by a streak plate method, and adding 50 mg/L spec and 50 mg/L Rif into an LB solid plate;

(b') selecting single plaques into 5 mL of an LB liquid medium containing 50 mg/L spec and 50 mg/L Rif, placing into a shaker at 28° C., and culturing at a shaking speed of 200 r/min for overnight (about 12-16 h);

(c') preserving strains, adding 750 μL of *Agrobacterium* solution to 250 μL of sterilized glycerol, and then storing in the refrigerator at −80° C. until use;

(d') shaking bacteria, adding 10 μL of spec with a concentration of 50 mg/L, 10 μL of Rif with a concentration of 50 mg/L and 10 μL of the *Agrobacterium* solution to 10 mL of the LB liquid medium, and culturing at 28° C., 200 r/min for overnight (about 12-16 h);

(e') when a concentration of the bacterial solution reaches OD600=1.5, adding 2 mL of the bacterial solution to the centrifuge tube, and centrifuging at a speed of 4000 r/min for 5 min;

(f') pouring off a supernatant, pipetting 1 mL of a new MS liquid medium, resuspending *Agrobacterium*, and centrifuging at a speed of 4000 r/min for 5 min;

(g') repeating the step of (f') once; and (h') after resuspending *Agrobacterium* with 1 mL of the new MS liquid medium, adding the resuspended *Agrobacterium* to 40 mL of MS liquid medium containing 40 μL of As with the concentration of 25 mg/L, obtaining the infestation solution, placing for more than 2 hours for infection;

wherein: 200 mL of the bacterial suspension comprises:
10 mL of 20× large amount of elements;
1 mL of 200× organic elements;
1 mL of 200× iron salt;
1 mL of 200× trace elements; and
5.6 g of sucrose;

(h) putting the leaves and the stems back to the pre-culture medium and co-culturing for 2-3 days at 28° C. in the dark, and forming plaques around the incisions of the leaves;

(i) washing bacteria, taking out the co-cultured leaves and stems, and washing for 5 times with sterile water supplemented with 500 mg/L Cef, wherein at a first time of washing, the co-cultured leaves and stems are placed on the shaker to shaking for 30 min, followed by 5 min each time to wash, so as to remove *Agrobacterium* on the surface of the co-cultured leaves and stems;

(j) taking out, drying with the filter paper, transferring to a tobacco bud medium, wherein the tobacco bud medium is MS+BA 1.0 mg/L+Kan 25 mg/L+Cef 500 mg/L, and a pH value is 5.8; observing after 2 weeks, wherein if no bacteria are found, the Cef concentration is reduced, if the bacteria are found, the Cef concentration is remained;

(k) changing the medium once every 2 weeks until adventitious buds are grown for generally 2 weeks, cutting off regenerated seedlings with a height of about 1 cm and transferring to the subculture medium MS+BA 0.2-0.1 mg/L+Kan 25 mg/L+Cef 500 mg/L with a pH value of 5.8;

(l) when the seedlings grow to the height of 2 cm with small buds, transferring to a rooting medium MS+NAA 0.2-0.1 mg/L, culturing at 24±1° C. under 12 h illumination, with an illumination intensity of 1500 lx for about 3 weeks, and growing thick root systems; and (m) when the root systems are grown to a length of 2-3 cm and the seedlings are about 7-10 cm in height, taking out of the triangular flask; washing the root culture medium; transplanting in a flower pot; and culturing in a greenhouse.

(3) Stable transgenic lines are obtained.

The genomic DNA of transgenic tobacco seedlings is extracted by Qiagen DNA extraction kit, a Kan resistance gene primer is designed for PCR amplification, positive plants are screened and 25 positive plants are detected.

The Kan resistance gene primer comprises:

```
                                          (SEQ ID NO: 7)
Kan F: 5'-TCTGGACGAAGAGCATCAGG-3',
and (SEQ ID NO: 8)
Kan R: 5'-ATGAATCCAGAAAAGCGGCC-3'.
```

Figure 4:
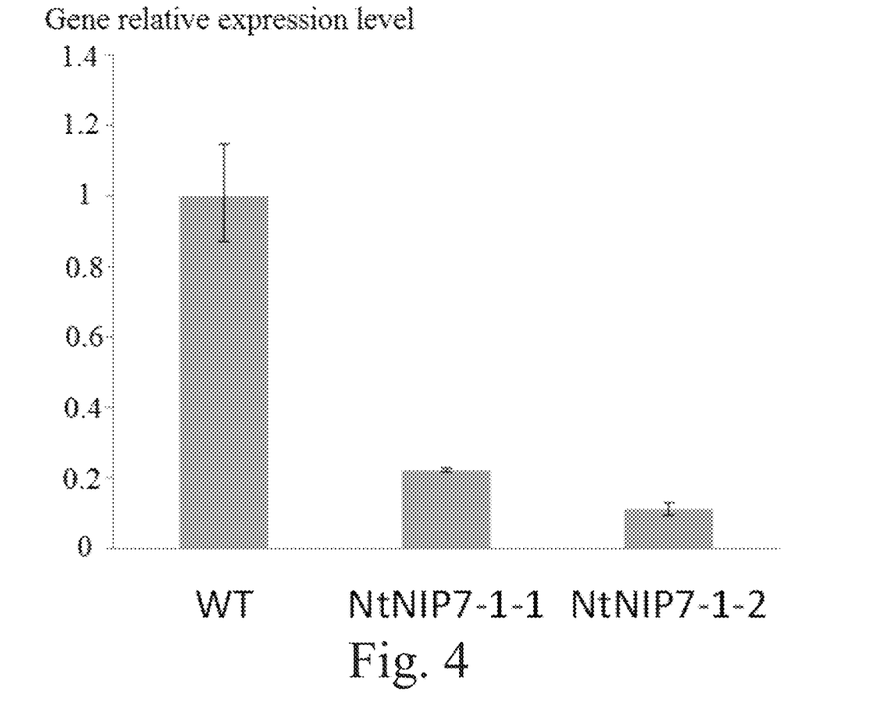
FIG. 4 is a histogram of the gene expression level of tobacco strains of NtNIP7-1 transgenic RNAi interference vector, wherein 'Yunyan 87' refers to wild type control, NtNIP7-1-1 and NtNIP7-1-2 are transgenic tobacco plants.
Figure 5:
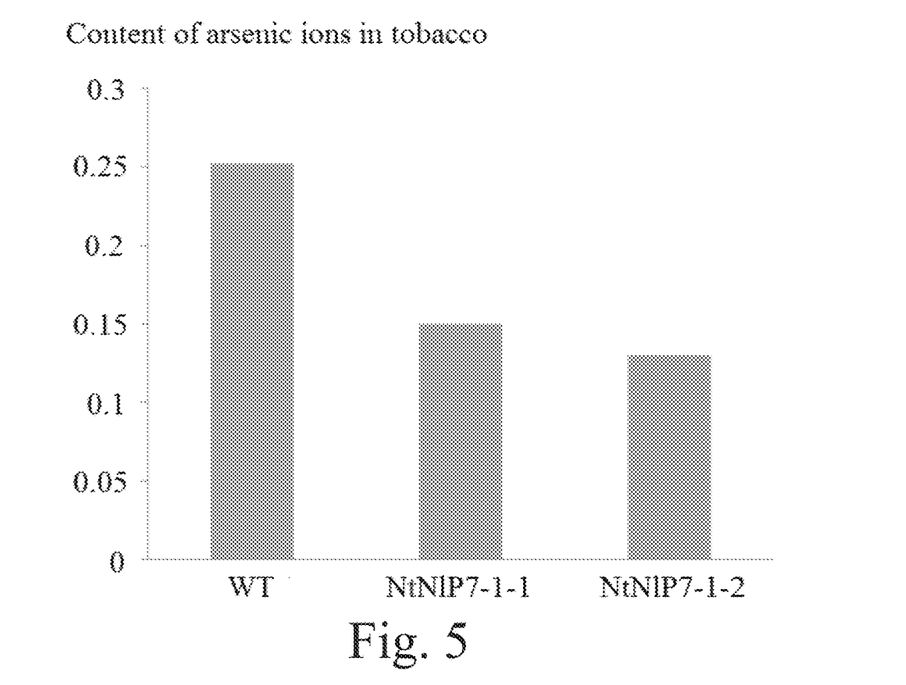
FIG. 5 is a schematic diagram showing the content of arsenic ions in tobacco interfered by NtNIP7-1 gene RNAi, wherein 'Yunyan 87' refers to wild type control, NtNIP7-1-1 and NtNIP7-1-2 are transgenic tobacco plants.

Total RNAs of Wild-type plants and 25 RNA gene T0 generation plants transformed with pHellsgate12 are extracted according to the method provided by the second embodiment of the present invention, and then are analyzed by Real time-PCR to analyze the expression of different lines, wherein the internal reference gene is 26 s. Two plants with the lowest expression are selected (referring to FIG. 4). Seeds are collected from each plant for respectively sowing, and the isolation of T1-generation plants is screened by Kan antibiotics. The above steps are repeated until the T3-generation obtains genetically stable transgenic lines.

The NtNIP7-1 qRT-PCR primer comprises:

```
                                          (SEQ ID NO: 9)
NtNIP7-1_qRT_F: 5'-AGGTCCAGTCTGTTGTGAGG-3';
and (SEQ ID NO: 10)
NtNIP7-1_qRT_R: 5'-TTTGCCTTAACCCGTTGAGC-3'.
```

The 26s internal reference gene primer comprises:

```
                                          (SEQ ID NO: 11)
26s_F: 5'-GAAGAAGGTCCCAAGGGTTC-3';
and (SEQ ID NO: 12)
26s_R: 5'-TCTCCCTTTAACACCAACGG-3'.
```

Fourth Embodiment

Determination of Arsenic Content in Tobacco:

Arsenic in tobacco is digested on an electric hot plate with nitric acid and perchloric acid, and then is measured by an atomic fluorescence spectrometer.

Devices are as follows:

AFS-9800 double channel atomic fluorescence spectrophotometer, GGX-6 atomic absorption spectrometer, AA-800 graphite furnace atomic absorption spectrometer, and balance with a sensitive quantity of 0.1 mg.

Working conditions of the devices are as follows:

The working conditions of the atomic fluorescence photometer are shown in Table 1.

TABLE 1

Working conditions of the atomic fluorescence photometer

| Conditions | As | Hg | Pb |
|---|---|---|---|
| Photomultiplier negative high voltage (V) | 280 | 280 | 280 |
| Lamp current (mA) | 60 | 15 | 50 |
| Atomization height (mm) | 8 | 8 | 8 |
| Flow of carrier gas (mL/min) | | 400 | |
| Flow of shielding gas (mL/min) | | 1000 | |
| Reading time (s) | | 12 | |

TABLE 1-continued

Working conditions of the atomic fluorescence photometer

| Conditions | As | Hg | Pb |
|---|---|---|---|
| Delay time (s) | | 2 | |
| Injection volume (mL) | | 1 | |
| Measurement method | | Std. Curve | |
| Reading method | | Peak. Area | |
| Injection procedure | | Automatic | |

Cadmium is measured by GGX-6 atomic absorption spectrometry. The working conditions of measuring cadmium are as follows. The wavelength is 228.8 nm, the lamp current is 6 mA, the slit has a width of 0.2 nm, the air flow is 5 L/min, the acetylene flow is 1.5 L/min, the integration time is 5 s, and the background correction method is Zeeman effect.

Nickel is measured by AA-800 graphite furnace atomic absorption spectrometry. The working conditions of measuring nickel are as follows. The wavelength is 283.3 nm, the slit has a width of 0.2 nm, the lamp current is in a range of 5 mA to 7 mA, the drying temperature is 120° C., the ashing is performed at 1100° C. for 20 s, the atomization is performed at 2300° C. for 4 s; the injection volume is 20 µL, and the background correction method is Zeeman effect.

The glassware comprises 250 mL flask, 250 mL curved neck funnel, 50 mL volumetric flask, 25 mL volumetric flask, 5 mL pipette, 10 mL pipette, 1 mL graduated pipette, 2 mL graduated pipette, 5 mL graduated pipette, and 10 mL graduated pipette.

The reagent comprises:

nitric acid, perchloric acid, 30% hydrogen peroxide, potassium borohydride, potassium ferricyanide, oxalic acid, thiourea, ascorbic acid and hydrochloric acid.

A preparation method of 2% potassium borohydride solution or 2% sodium borohydride solution and 0.5% sodium hydroxide solution comprises diluting 20 g potassium borohydride or 20 g sodium borohydride and 5 g sodium hydroxide to 1000 mL with water.

A preparation method of a dihydrate oxalic acid solution with a concentration of 10 g/L comprises weighing 1.0 g of oxalic acid dihydrate, dissolving in an appropriate amount of water, and diluting to 100 mL with water, wherein the dihydrate oxalic acid solution is prepared on site.

A preparation method of a potassium ferricyanide solution with a concentration of 100 g/L comprises weighing 10 g of potassium ferricyanide, dissolving in an appropriate amount of water, and diluting to 100 mL with water, wherein the potassium ferricyanide solution is prepared on site.

Experimental water is deionized water.

Steps are analyzed as follows:

Pretreatment of arsenic in a tobacco sample:

Weighing 1 g (accurate to 0.0001 g) of the tobacco sample which is dried at 40° C. and pulverized through a 40-mesh sieve; putting the tobacco sample into a 150 mL erlenmeyer flask, adding 10 mL of nitric acid and 2 mL of perchloric acid, covering with a small curved neck funnel, immersing for 8 h or placing for overnight, heating on the electric hot plate for digesting till a white material occurs, taking down and cooling down, washing the wall of the erlenmeyer flask with a little water, adding 2.5 mL hydrochloric acid, heating to the boiling, taking down and cooling down, transferring to a 25 mL volumetric flask, diluting to the scale with water, shaking well, and obtaining a standby solution. Taking 10 mL of the standby solution into a 10 mL test tube (which is dried), adding 0.1 g of thiourea and 0.1 g of ascorbic acid, shaking well, placing for 4 h, testing within 24 h for measuring arsenic by the atomic fluorescence spectrometer, and simultaneously acting as a reagent blank. Taking 5 mL of the standby solution into a 50 mL volumetric flask, adding 1.0 mL of an oxalic acid dihydrate solution with a concentration of 10 g/L and 3.0 mL of a potassium ferricyanide solution with a concentration of 100 g/L, diluting to the scale with 1% hydrochloric acid, and shaking well for the atomic fluorescence spectrophotometer measuring lead and simultaneously acting as a reagent blank.

Determination is as follows.

According to the content of the sample, preparing the sample solution with different concentrations (acid conditions and other reagents and samples are the same conditions), adjusting the lamp position, preheating for about 30 min under the set instrument working conditions, and measuring the standard working curve after ignition. The determination is performed by an atomic fluorescence spectrometer.

Result calculation is as follows.

Calculating the arsenic content according to the following formula of:

$$X \text{ (mg/kg)} = \frac{V \times A \times C}{M \times 1000}$$

wherein:
X refers to arsenic in the tobacco sample, mg/kg;
V refers to the volume of the sample digestion, mL;
A refers to the dilution factor of the sample;
C refers to the concentration of the sample solution, µg/L;
M refers to the weight of the sample, g.

The arsenic content of the transgenic plants is found to be reduced by about 36% compared with the non-transgenic material, indicating that the NtNIP7-1 gene is able to affect the arsenic content in tobacco.

What is claimed is:

1. A preparation method of a low arsenic transgenic plant, which comprises inhibiting an expression of a tobacco arsenic transport gene NtNIP7-1 in tobacco plants by directly targeting a nucleotide sequence of the tobacco arsenic transport gene NtNIP7-1 or RNA encoded by the tobacco arsenic transport gene NtNIP7-1, wherein the nucleotide sequence of the tobacco arsenic transport gene NtNIP7-1 comprises SEQ ID NO: 1.

2. A preparation method of a low arsenic transgenic plant, which comprises inhibiting an expression of a tobacco arsenic transport gene NtNIP7-1 in tobacco plants by directly targeting a nucleotide sequence of the tobacco arsenic transport gene NtNIP7-1 or RNA encoded by the tobacco arsenic transport gene NtNIP7-1, wherein an amino acid sequence encoded by the tobacco arsenic transport gene NtNIP7-1 comprises SEQ ID NO: 2.

* * * * *